United States Patent [19]

Rosellini

[11] Patent Number: 5,192,207
[45] Date of Patent: Mar. 9, 1993

[54] COMPOSITE RESIN CROWN, REPLACEMENT TOOTH AND METHOD

[76] Inventor: Davey G. Rosellini, 1950 Balearic Dr., Costa Mesa, Calif. 92626

[21] Appl. No.: 760,980

[22] Filed: Sep. 17, 1991

[51] Int. Cl.[5] .............................................. A61C 5/10
[52] U.S. Cl. .................................. 433/223; 433/203.1; 433/212.1; 433/218; 433/40; 264/19
[58] Field of Search ...................... 433/223, 218, 212.1, 433/202.1, 40, 203.1, 219, 220, 215, 26; 264/16, 19, 20

[56] References Cited

U.S. PATENT DOCUMENTS

| | | | |
|---|---|---|---|
| 4,203,515 | 5/1980 | Kahn et al. | 433/218 |
| 4,678,435 | 7/1987 | Long | 433/218 |
| 4,778,386 | 10/1988 | Spiry | 433/223 |
| 4,810,193 | 3/1989 | Wieder | 433/26 |

FOREIGN PATENT DOCUMENTS 0087022  8/1983  European Pat. Off. .............. 433/40

*Primary Examiner*—John J. Wilson
*Attorney, Agent, or Firm*—Walter A. Hackler

[57] ABSTRACT

A crown and/or a replacement tooth and a method of in situ production thereof by grinding and shaping a tooth to form a prepared tooth; filling a transparent shell tooth form with a light setting resin; disposing the filled shell tooth form onto the prepared tooth; illuminating the filled transparent shell tooth form to set the light setting resin and bond the resin to the shell tooth form; and shaping and polishing the set resin in situ to form a crown. A set of shell tooth forms is provided which are formed from a light setting resin chemically compatible with the resin used to fill the form in order that bonding occurs therebetween. This feature enables the products of a replacement tooth formed in situ without the necessity of shell tooth form removal as heretofore required.

22 Claims, 2 Drawing Sheets

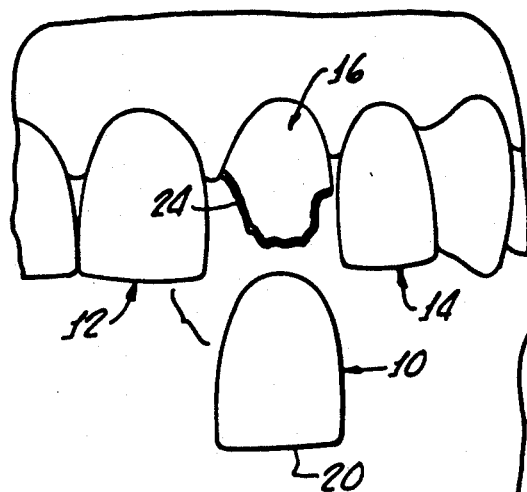
Fig. 1.
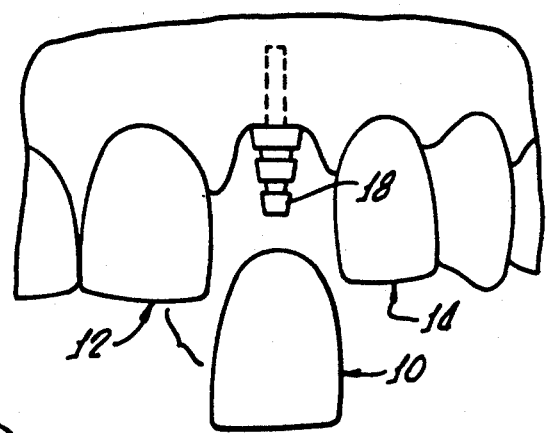
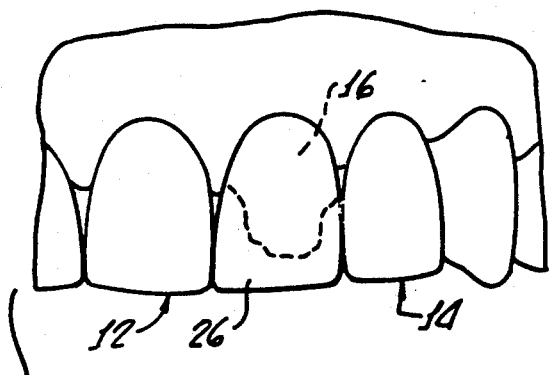
Fig. 2.
Fig. 3.

COMPOSITE RESIN CROWN, REPLACEMENT TOOTH AND METHOD

The present invention generally relates to artificial teeth and crowns and, more particularly, relates to the in situ production of artificial teeth and crowns and shell tooth forms therefor.

Heretofore, artificial teeth and crowns have been made from metal, porcelain, combinations of metal and porcelain, and resins.

Crowns made of precious or semi-precious metal are expensive and the luster inherent in the metal does not match well with the existing teeth and body tissue and is therefore not desirable.

Porcelain crowns have been utilized and are typically produced from casts from the actual tooth location. However, the firing of porcelain causes dimensional changes therein and hence, the finished tooth may not properly fit the patient. Because this type of artificial tooth requires high technology of porcelain building and firing and must have high dimensional accuracy, the production cost thereof is very high.

Combinations of metal and porcelain in which the porcelain is built and baked on the crown surface to shade the luster of the metal crown have been found to be complicated and also expensive to produce.

All of the hereinabove described artificial teeth and crowns require a laboratory necessary for the fabrication of the tooth and crown. As a result, the procedure becomes expensive due to repeated visits to the dental office for refitting and additional procedural steps for the dentist.

In connection therewith, and also as an independent source of artificial crowns and teeth, is the technology built around newly-developed resins and epoxies or the like which are quick-setting. In this procedure the resin is disposed in a mold and inserted in a tooth. After a period of time the mold with partially set resin is removed from the patient's mouth and shaped by the dentist. Subsequent to continued hardening of the resin, it is cemented in place in the patient's mouth and thereafter finished by polishing. Unfortunately, the form, when removed, leaves the cast tooth undersized.

The method of the present invention enables the in situ formation of an artificial tooth or crown useful in restoring a tooth or replacing a tooth. Because of the in situ formation and shaping of the crown or tooth, repeated visits to a dental office and the subcontracting of work to a dental laboratory are eliminated. This result is significant time and cost savings for the patient. However, if a porcelain type crown is preferred, the method of the present invention is useful in providing a temporary crown which may be utilized in a traditional manner while the porcelain type crown is manufactured.

SUMMARY OF THE INVENTION

A method of making a permanent crown for a tooth in accordance with the present invention generally includes the steps of grinding and shaping the tooth to form a prepared tooth in order to provide anchorage for the restoration resin.

After tooth preparation, a transparent shell tooth form is filed with a photopolymerizable, or light setting, resin. The filled shell is thereafter disposed on the prepared tooth and illuminated through the transparent shell tooth form to set the light setting resin and bond the light setting resin to the shell tooth form. Preferably, the shell tooth form is made from the same light setting resin used to fill the tooth form. This insures good bonding therebetween. Thereafter, the tooth form is shaped and polished in situ to form the permanent crown.

Alternatively, the method of the present invention is suitable for the forming of an artificial tooth. In this procedure, a post is set in the patient's jaw in a conventional manner and thereafter, a transparent shell tooth with a light setting resin is disposed thereover.

As hereinabove described, thereafter, the form, with resin, is illuminated to set the resin. The shell is then shaped and polished to a finished product in the dental office.

A temporary crown may also be made if the prepared tooth is coated with a substance preventing bonding of the light setting resin thereto. In this instance, the temporary crown is removed after setting the resin and thereafter cemented to the prepared tooth.

An important embodiment of the present invention includes the step of disposing a second light setting resin within the transparent shell tooth form to encase inside surfaces thereof. In utilizing a second light setting resin having a different color from the primary light setting resin, shading of the tooth to make existing teeth is available. For example, the second light setting resin may be disposed at a position enabling the crown to have a gum line color different from a body color. Alternatively, the second light setting resin may be disposed in the shell to form a position enabling the crown to have a shaded body color.

Because a transparent shell tooth form is utilized, the dentist can observe the color match of the combined resins within the shell in situ to ensure color match with adjacent teeth. It should be appreciated that while the present invention is discussed in terms of two light setting resins, any number may be utilized in order to obtain satisfactory tooth coloring.

When the color match is satisfactory, the resin is permeated to cause setting thereof with the color shading remaining intact.

The present invention also includes a crown and a replacement tooth made by the hereinabove described methods.

In addition to the hereinabove recited steps, the present invention importantly may include the step of adding light setting resin to an exterior of the shell tooth form and illuminating the added light setting resin to bond it to the shell tooth form. In this manner, the crown or replacement tooth may be further shaped and sized to fit the patient.

Also included in the present invention is one or more, preferably a set of shell tooth forms made from light setting resin.

BRIEF DESCRIPTION OF THE DRAWINGS

The advantages and features of the present invention will appear from the following description, when considered in conjunction with the accompanying drawings in which:

FIG. 1 is a representation of a prepared broken tooth and a transparent shell tooth form of appropriate size to be filled with a light setting resin and disposed over the prepared broken tooth;

FIG. 2 is a similar to FIG. 1 showing the shell tooth form for use over an implanted endodontic post for forming a replacement tooth;

FIG. 3 shows the step of illuminating a filled shell tooth form, disposed over the prepared tooth shown in FIG. 1, in order to set the resin therein;

DETAILED DESCRIPTION

Figure 4:
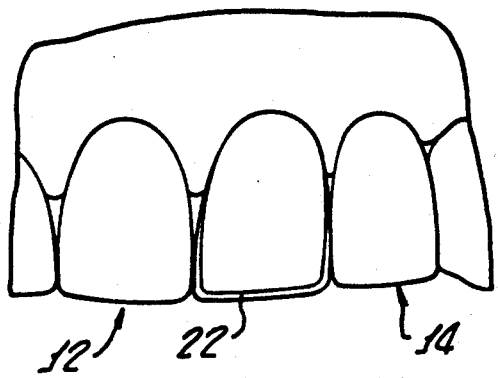
FIG. 4 illustrates the step of adding light setting resin to an exterior of the shell tooth form.

It should be appreciated that the method of the present invention may utilize and encompass an entire set of transparent shell tooth forms 10 suitable for matching in a reasonable manner the tooth shapes found in most patients. In combination with this set of forms is a plurality of photopolymerizable materials, light setting resins, for use with a light gun for illuminating the resin (typically with ultraviolet light). Importantly, the set of shell tooth forms are made from the same, or chemically compatible, resins as that used to fill the forms in order that bonding occurs therebetween. The shell tooth form may be made from the light setting resin by coating a tooth mold with the resin, setting of the resin by illumination thereof, and removal of the set resin from the form, thus producing a shell tooth form. Suitable light setting resins are Prisma A.H., Silux Plus, Herculite, Durafill which are available from any dental supplier. The thickness of the coating should be selected so that the resultant shell-tooth forms have sufficient strength to permit filling of the shell tooth form 10 with resin without deformation of the shell tooth form. In this regard, the shell tooth form may be made by repeated coating of resin and sequential illuminating thereof in order to produce a desired shell tooth form thickness.

As shown in FIG. 1, the crown form 10 is selected to match adjacent teeth 12, 14 and fit over a prepared tooth 16, the latter being prepared in the conventional manner by grinding and shaping to form a support for the crown form in accordance with the method of the present invention. Alternatively, the crown form 10 may be disposed over a post 18 as shown in FIG. 2, the post 18 being implanted in a conventional manner prior to the procedures of the present invention.

The margin 20 of the form may be contoured and adjusted in size to ensure proper sizing of the crown formed by the present method.

Thereafter, the form 10 is filled with a light setting resin 26 which may be of any conventional type for anterior or posterior use such as Prisma A.H, Silux Plus, Herculite, Durafill, or the like, available from any dental suppliers.

Upon filling of the mold, it is disposed onto the prepared tooth 16 and illuminated through the transparent shell form 10 by a conventional light emitting source 30, FIG. 3.

As shown in FIG. 4, additional light setting resin 22 may be added to the shell tooth form 10 in order to build the size, both length and width, thereof as may be necessary to produce a properly sized and shaped tooth. This is made possible by the use of a resin 32 which is the same or chemically compatible with the sell tooth form 10 in order that bonding occurs upon setting of the resin 32. Thereafter, the shell form and added resin 22 is illuminated to set the additional resin 22 and polished to form a permanent crown.

Additionally, if a coating, such as a vaseline 24, or the like, is disposed on the prepared tooth 16, see FIG. 1, the shell form 10 may be removed after setting of the resin to produce a temporary crown which may be later cemented to the prepared tooth while awaiting the fabrication and filling of a porcelain type crown (not shown).

Figure 5:
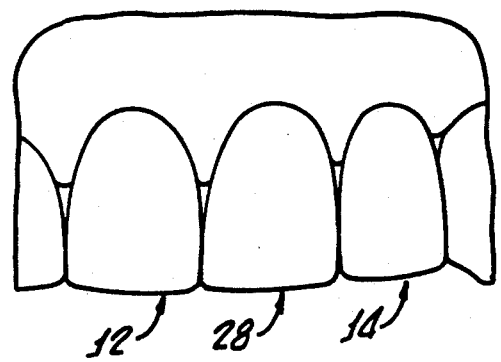
FIG. 5 illustrates a completed crown or replacement tooth.

The procedures hereinabove described may be utilized in combination with the post 18 conventionally disposed in the patient's jaw for receiving the form 10 and resin, as shown in FIG. 2. The finished replacement tooth 28 is shown in FIG. 5.

Figure 6:
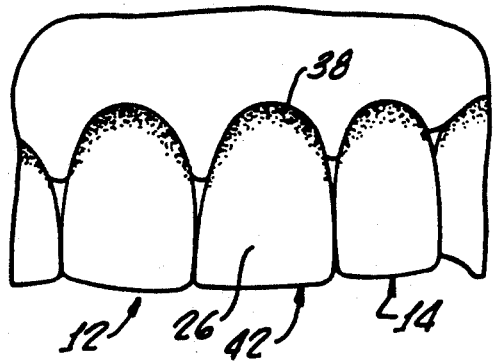
FIGS. 6 and 7 illustrate how two different color light setting resins may be used to provide a finished crown or replacement tooth having a different gingival color, FIG. 6, or shaded colors, FIG. 7, in different incisal and body colors, in order to in situ match the coloring of adjacent teeth.
Figure 7:
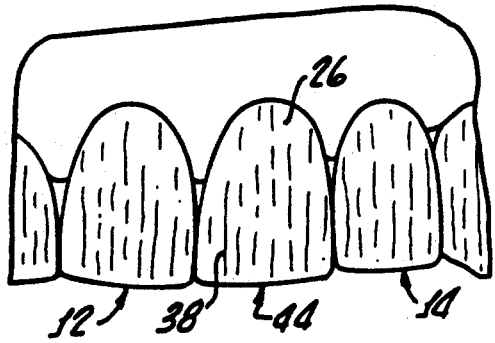

Alternatively, as shown in FIGS. 6 and 7, a second light setting resin 38 may be disposed within a shell tooth form adjacent an interior surface thereof in order to change the color pattern of the finished crown 42. As shown in FIG. 6, the second light setting material may be disposed in a position in order that the crown 42 has a gingival color different from the body color as represented by the shading of the crown 42.

As shown in FIG. 7, the second light setting resin may be disposed in a shell in the form 10 in a position enabling the finished crown 44 to have a shaded body color with an incisal color different from a body color. It should be appreciated that although two light setting resins are discussed herein which have different coloration, any number of light setting colors can be utilized to produce a crown or replacement tooth in accordance with the present invention with a shaded coloring.

Importantly, the shading and coloration of each individual crown or tooth may be determined and changed to match adjacent teeth before setting of the light setting resins. Additional color shading may be provided by applying added resin 22 of a different color as described in connection with FIG. 4.

This enables the dental practitioner to satisfactorily design the tooth coloration by repeated removal and changing of the light setting resins within tooth form before irradiation thereof and final color matching by the addition of resin to the exterior of the tooth form 10. This procedure may include the coating of the entire labial surface of the tooth form, or tooth, as a veneer to alter the color or shape of the final tooth.

This has a significant advantage over prior art systems in which colorations were not possible in situ situations. Heretofore, only color charts could be utilized and because a separate laboratory was used to manufacture replacement teeth and crowns, there could be no side-by-side comparison of the proposed unset crown or replacement tooth with adjacent existing teeth.

Although there has been hereinabove described a COMPOSITE RESIN CROWN, REPLACEMENT TOOTH AND METHOD in accordance with the present invention, for the purposes of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A method of making a permanent crown for a tooth comprising:
   grinding and shaping the tooth to form a prepared tooth;

filling a transparent shell tooth form with a light setting resin;

disposing the filled shell tooth form onto the prepared tooth;

illuminating the filled transparent shell tooth form to set the light setting resin therein and bond the light setting resin to the shell tooth form and prepared tooth; and shaping and polishing the shell tooth form in situ to form a crown.

2. The method of claim 1 further comprising the steps of adding light setting resin to an exterior of the shell tooth form and illuminating the added light setting resin to bond it to the shell tooth form exterior.

3. The method of claim 1 further comprising the steps of adding a light setting resin of a different color than the light setting resin within the shell tooth form to an exterior of the shell tooth form and illuminating the added light setting resin to bond it to the shell tooth form exterior.

4. The method of claim 1 further comprising the step of disposing a second light setting resin within the transparent shell tooth form adjacent inside surfaces thereof, said second light setting resin having a different color from said light setting resin.

5. The method of claim 4 wherein said second light setting resin is disposed in said shell tooth form at a position enabling the crown to have a gum line color different from a body color.

6. The method of claim 4 wherein said second light setting resin is disposed in said shell tooth form at a position enabling the crown to have a shaded body color.

7. The method of claim 4 further comprising the steps of observing a color pattern of the light setting resins through the transparent shell tooth form while the shell tooth form is disposed over the prepared tooth, removing the filled shell tooth form to change the color pattern by addition and/or removal of the light setting resins and replacing the filled tooth form into the prepared tooth before setting of the light setting resins.

8. A method of making a permanent replacement tooth comprising:

setting a post in a patient's jaw;

filling a transparent shell tooth form with a light setting resin;

disposing the filled shell tooth form onto the post;

illuminating the filled transparent shell tooth form to set the light setting resin therein and bond the light setting resin to the shell tooth form and post; and shaping and polishing the shell tooth form in situ to form a replacement tooth.

9. The method of claim 8 further comprising the steps of adding light setting resin to an exterior of the shell tooth form and illuminating the added light setting resin to bond it to the shell tooth form exterior.

10. The method of claim 8 further comprising the steps of adding a light setting resin of a different color than the light setting resin within the shell tooth form to an exterior of the shell tooth form and illuminating the added light setting resin to bond it to the shell tooth form exterior.

11. The method of claim 8 further comprising the step of disposing a second light setting resin within the transparent shell tooth form adjacent inside surfaces thereof, said second light setting resin having a different color from said light setting resin.

12. The method of claim 11 wherein said second light setting resin is disposed in said shell tooth form at a position enabling the crown to have a gum line color different from a body color.

13. The method of claim 11 wherein said second light setting resin is disposed in said shell tooth form at a position enabling the crown to have a shaded body color.

14. The method of claim 11 further comprising the steps of observing a color pattern of the light setting resins through the transparent shell tooth form while the shell tooth form is disposed over the post, removing the filled shell tooth form to change the color pattern by addition and/or removal of the light setting resins and replacing the filled tooth form into the post before setting of the light setting resins.

15. A permanent crown for a tooth made by:

grinding and shaping the tooth to form a prepared tooth;

filling a transparent shell tooth form with at least one light setting resin;

disposing the filled shell tooth form onto the prepared tooth;

illuminating the filled transparent shell tooth form to set the light setting resin and bond the light setting resin to the shell tooth form; and shaping and polishing the shell tooth form in situ to form the permanent crown; and adding light setting resin to an exterior of the shell tooth form and illuminating the added light setting resin to bond it to the shell tooth form exterior.

16. The permanent crown of claim 15 made by the additional steps of adding a light setting resin of a different color than the light setting resin within the shell tooth form to an exterior of the shell tooth form and illuminating the added light setting resin to bond it to the shell tooth form exterior.

17. The crown according to claim 15 comprised of two light setting resins having different color and disposed relative to one another so that the crown has a gum line color different from a body color.

18. The crown according to claim 15 comprised of two light setting resins having different color and disposed relative to one another so that the crown has a shaded body color.

19. A replacement tooth made by:

setting a post in a patient;

filling a transparent shell tooth form with a light setting resin;

disposing the filled shell tooth form onto the post;

illuminating the filled transparent shell tooth form to set the light setting resin and bond the light setting resin to the shell tooth form and post;

shaping and polishing the shell tooth form in situ to form a replacement tooth; and adding light setting resin to an exterior of the shell tooth form and illuminating the added light setting resin to bond it to the shell tooth form exterior.

20. The replacement tooth of claim 19 made by the additional steps of adding a light setting resin of a different color than the light setting resin within the shell tooth form to an exterior of the shell tooth form and illuminating the added light setting resin to bond it to the shell tooth form exterior.

21. The replacement tooth of claim 19 comprised of two light setting resins having different color and disposed relative to one another so that the replacement tooth has a gum line color different from a body color.

22. The replacement tooth of claim 19 comprised of two light setting resins having different colors and disposed relative to one another so that the replacement tooth has a shaded body color.

* * * * *